(12) United States Patent
Jan

(10) Patent No.: US 9,388,266 B2
(45) Date of Patent: Jul. 12, 2016

(54) FLUORO-CONTAINING ETHER MONOMER FOR FABRICATING CONTACT LENSES, CONTACT LENSES MATERIALS AND CONTACT LENSES OBTAINED THEREFROM

(71) Applicant: BenQ Materials Corporation, Taoyuan (TW)

(72) Inventor: Fan-Dan Jan, Taoyuan (TW)

(73) Assignee: BenQ Materials Corporation, Taoyuan (TW)

(*) Notice: Subject to any disclaimer, the term of this patent is extended or adjusted under 35 U.S.C. 154(b) by 0 days.

(21) Appl. No.: 14/640,036

(22) Filed: Mar. 6, 2015

(65) Prior Publication Data
US 2015/0177418 A1  Jun. 25, 2015

Related U.S. Application Data

(62) Division of application No. 13/917,656, filed on Jun. 14, 2013, now Pat. No. 9,221,939.

(51) Int. Cl.
| | |
|---|---|
| C08F 230/08 | (2006.01) |
| G02B 1/04 | (2006.01) |
| C08F 226/08 | (2006.01) |
| C07C 271/24 | (2006.01) |
| G02C 7/04 | (2006.01) |

(52) U.S. Cl.
CPC .............. *C08F 230/08* (2013.01); *C07C 271/24* (2013.01); *C08F 226/08* (2013.01); *G02B 1/043* (2013.01); *G02C 7/049* (2013.01)

(58) Field of Classification Search
CPC .............................. C08F 226/08; G02C 7/049
See application file for complete search history.

(56) References Cited

U.S. PATENT DOCUMENTS

| | | | |
|---|---|---|---|
| 5,084,537 A | 1/1992 | Stoyan | |
| 5,302,678 A | 4/1994 | Nomura et al. | |
| 8,952,080 B2 * | 2/2015 | Jan | ........................ C08F 230/08 523/107 |
| 2002/0005933 A1 | 1/2002 | Imafuku | |
| 2013/0056889 A1 * | 3/2013 | Jan | ........................ G02B 1/043 264/1.1 |

FOREIGN PATENT DOCUMENTS

| | | |
|---|---|---|
| CN | 103360591 A | 10/2013 |
| EP | 0425436 A2 | 5/1991 |
| JP | S62-501781 A | 7/1987 |
| JP | 03-153726 A | 7/1991 |
| JP | 04321660 A | 11/1992 |
| JP | 06-043408 A | 2/1994 |
| JP | 06-289332 A | 10/1994 |
| JP | 07-181435 A | 7/1995 |
| JP | 2793363 B2 | 9/1998 |
| TW | 200927792 | 7/2009 |
| TW | 201303001 A1 | 1/2013 |
| TW | 201312201 A1 | 3/2013 |
| WO | 2014/053636 A1 | 4/2014 |

OTHER PUBLICATIONS

Maio et al., "Fluorinated hyperbranched polyester acrylate used as an additive for UV curing coatings", Progress in Organic Coatings, 2009, 65, 71-76.*

* cited by examiner

*Primary Examiner* — Nicole M Buie-Hatcher
(74) *Attorney, Agent, or Firm* — CKC & Partners Co., Ltd.

(57) ABSTRACT

The invention provides a fluoro-containing ether monomer for fabricating contact lenses represented by following formula (I):

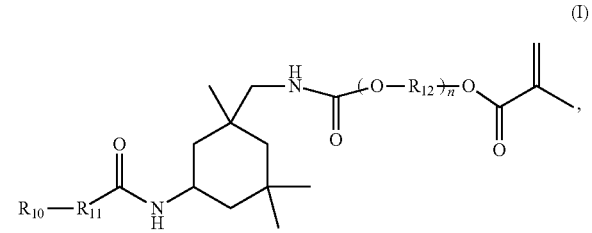

In formula (I), $R_{10}$ is fluoroalkyl group $(C_xF_yH_z)$, wherein x is an integer of 2-20, y is an integer of 5-30, and y+z=2x-1), $R_{11}$ is oxygen, nitrogen or sulfur; $R_{12}$ is $C_1$-$C_3$ alkylene; n is an integer of 3-40.

5 Claims, No Drawings

FLUORO-CONTAINING ETHER MONOMER FOR FABRICATING CONTACT LENSES, CONTACT LENSES MATERIALS AND CONTACT LENSES OBTAINED THEREFROM

CROSS-REFERENCE TO RELATED APPLICATION

The present application is a Divisional application of the application Ser. No. 13/917,656 filed Jun. 14, 2013, the entire contents of which are hereby incorporated herein by reference.

BACKGROUND

1. Technical Field

The present invention relates to a composition for fabricating contact lenses. More particularly, the composition for fabricating contact lenses comprising a fluoro-containing ether monomer.

2. Description of Related Art

In the early years hard contact lenses were mainly made of glass. The soft contact lenses were therefore developed to improve the discomfort of wearing of the hard contact lenses. The soft contact lenses can be classified into two categories, hydrogel contact lenses and silicone hydrogel contact lenses.

The hydrogel contact lenses are made from hydrogel materials, such as poly-2-hydroxyethyl methacrylate (p-HEMA). Since the water content of the p-HEMA is only about 38.8%, one or more than one kinds of the hydrophilic monomer, for example N-vinylpyrrolidone (NVP), N,N-dimethylacrylamide (DMA) and methyl acrylic acid (MAA), are added to enhance the water content of such materials for the contact lenses.

With the addition of the hydrophilic monomer, the water content of the contact lenses can increase up to 80%. However, the higher water content of the contact lens is, the lower tension and toughness thereof become. Therefore, the water content of contact lenses is generally controlled in the range from about 45% to 58% to have a sufficient mechanical strength for the contact lenses.

For improving the disadvantages of the hydrogel contact lenses, silicone contact lenses with excellent oxygen permeability (DK) have been studied for a number of years. The silicone hydrogel contact lenses are made by polymerizing a hydrophilic silicone polymeric material and a hydrophilic monomer.

However, the lipid secreted from the human eyes would produce lipid deposition on the contact lenses and result in discomfort when wearing. It is known in the prior art that the fluorosilicone acrylate is suitable for manufacturing contact lenses because of having high oxygen permeability, which can reduce corneal disease from hypoxia. In addition, the contact lenses also provide comfort of wearing and not to absorb ocular secretions. But the disadvantage of the contact lenses is poor in flexibility.

Thus, the present invention provides a novel fluoro-containing ether monomer for fabricating contact lenses and the contact lenses fabricating therefrom have desirable physical properties and is comfortable in wearing.

SUMMARY

Proteins in the tears are easily absorbed on the surface of the contact lenses, which may induce lipid deposition thereon. The present invention provides a fluoro-containing ether monomer for fabricating contact lenses which can prevent such lipid deposition, provide the comfort of wearing and have better oxygen permeability (DK).

According to an aspect of the present invention, the fluoro-containing ether monomer for fabricating contact lenses is provided. The fluoro-containing ether monomer is represented by the following formula (I):

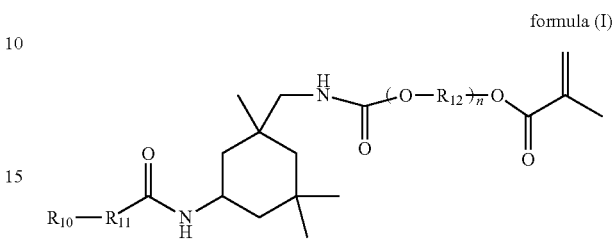

formula (I)

wherein $R_{10}$ is fluoroalkyl group ($C_xF_yH_z$, wherein x is an integer of 2 to 20, y is an integer of 5 to 30, and $y+z=2x+1$); $R_{11}$ is oxygen, nitrogen or sulfur; $R_{12}$ is $C_1$-$C_3$ alkylene group and n is an integer of 3 to 40.

The present fluoro-containing ether monomer for fabricating contact lenses can be used in hydrogel contact lenses and in silicone hydrogel contact lenses. Thus, a composition for fabricating contact lenses is provided. According to an aspect of the present invention, the composition for fabricating contact lenses comprises: a fluoro-containing ether monomer represented by the following formula (I):

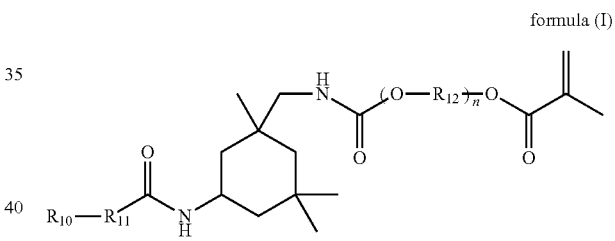

formula (I)

wherein $R_{10}$ is fluoroalkyl group ($C_xF_yH_z$, wherein x is an integer of 2 to 20, y is an integer of 5 to 30, and $y+z=2x+1$); $R_{11}$ is a oxygen, nitrogen or sulfur; $R_{12}$ is $C_1$-$C_3$ alkylene group; and n is an integer of 3 to 40; at least one hydrophilic monomer; at least one siloxane macromer and an initiator.

According to another aspect of the present invention, the composition for fabricating contact lenses comprises a fluoro-containing ether monomer represented by the above formula (I); at least one hydrophilic monomer and an initiator.

The above and other aspects of the invention will become better understood with regard to the following detailed description of the preferred but non-limiting embodiment(s).

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

The present invention provides a composition for fabricating contact lenses that can prevent from lipid deposition, provide better oxygen permeability and adequate water content.

According to an aspect of the present invention, a fluoro-containing ether monomer for fabricating contact lenses is provided. The fluoro-containing ether monomer is represented by the following formula (I):

formula (I)

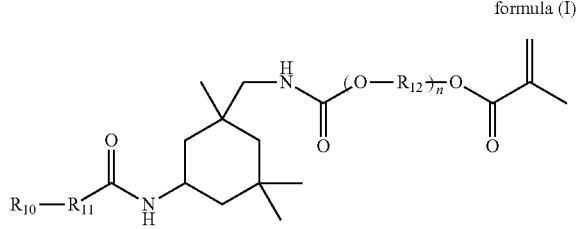

wherein, $R_{10}$ is fluoroalkyl group ($C_xF_yH_z$, wherein x is an integer of 2 to 20, y is an integer of 5 to 30, and y+z=2x+1); $R_{11}$ is a oxygen, nitrogen or sulfur; $R_{12}$ is $C_1$-$C_3$ alkylene group and n is an integer of 3 to 40.

In an embodiment of the present invention, the molar ratio of fluorine to carbon in fluoro-containing ether monomer is in the range of 0.032 to 0.88. Moreover, the fluoro-containing ether monomer is present at an amount of 0.07 to 0.4 weight percent based on the total amount of the contact lenses.

In an embodiment of the present invention, the fluoro-containing ether monomer is represented by the following formula (I-1), wherein $R_{10}$ is $C_5F_5H_6$; $R_{11}$ is oxygen, $R_{12}$ is $CH_2CH_2$ and n is n is an integer of 3 to 40.

formula (I-1)

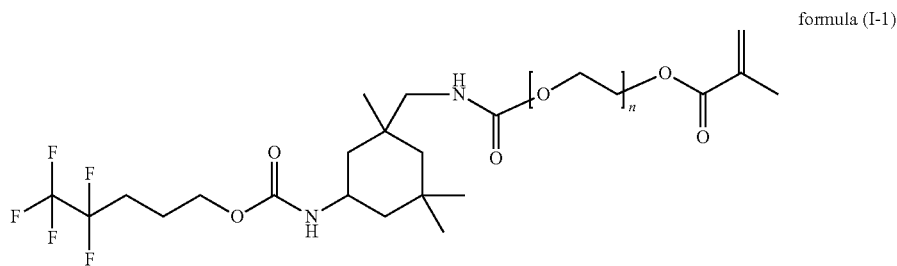

In an embodiment of the present invention, the fluoro-containing ether monomer is represented by the following formula (I-2), wherein $R_{10}$ is $C_{10}F_{17}H_4$, $R_{11}$ is oxygen, $R_{12}$ is $CH_2CH_2$ and n is n is an integer of 3 to 40.

formula (I-2)

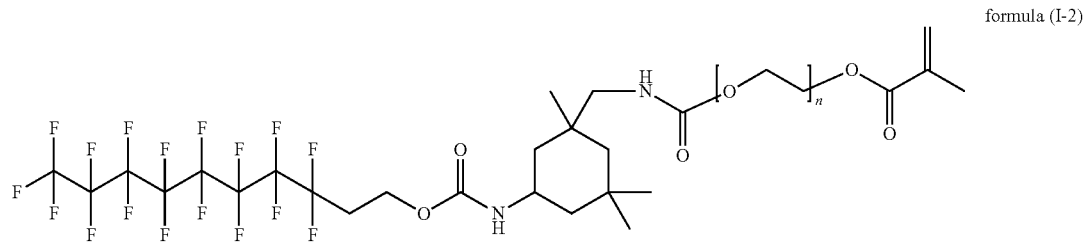

In an embodiment of the present invention, the fluoro-containing ether monomer is represented by the following formula (I-3), wherein $R_{10}$ is $C_{10}F_{17}H_4$, $R_{11}$ is sulfur, $R_{12}$ is $CH_2CH_2$ and n is n is an integer of 3 to 40.

formula (I-3)

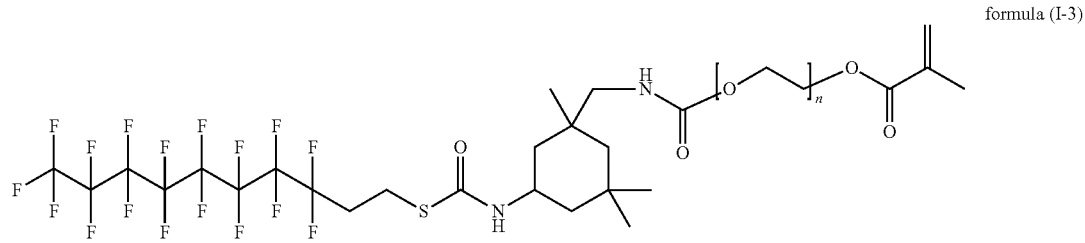

According to an aspect of the present invention, a composition for fabricating contact lenses comprises a fluoro-containing ether monomer represented by the formula (I); at least one siloxane macromer; at least one hydrophilic monomer and an initiator.

In an embodiment of the present invention, the siloxane macromer comprises a first siloxane macromer and a second siloxane macromer, The first siloxane macromer is represented by the following formula (II) or a siloxane macromer represented by the following formula (III):

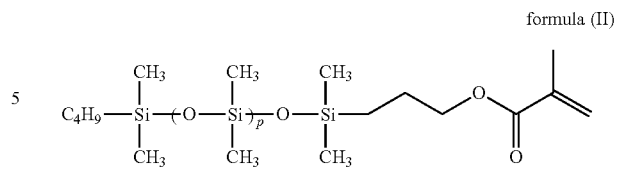

formula (II)

wherein in formula (II), p is an integer of 4 to 80,

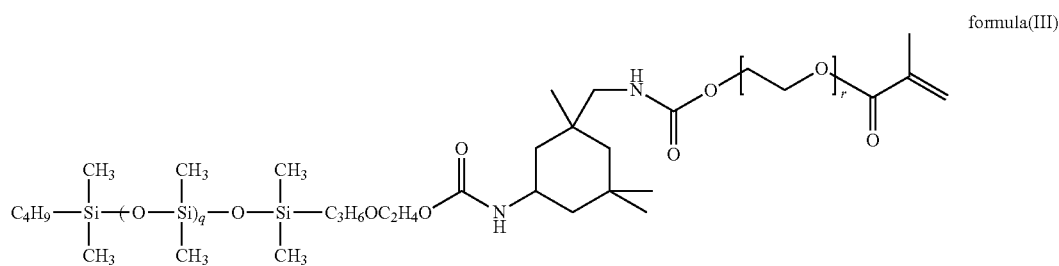

formula(III)

wherein in formula (III), q is an integer of 4 to 80 and r is an integer of 3 to 40. The second siloxane macromer represented by the following formula (IV), with the number average molecular weight of 1,000 to 10,000 and the second siloxane macromer has cross-linking functional groups;

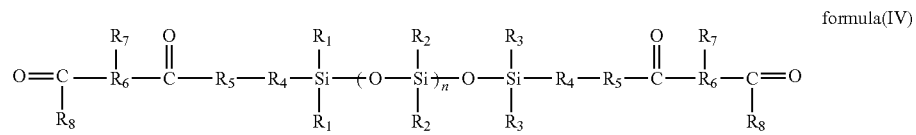

formula(IV)

wherein $R_1$, $R_2$ and $R_3$ are independently $C_1$-$C_4$ alkyl groups, $R_4$ is $C_1$-$C_6$ alkenylene group, $C_1$-$C_6$ alkylene group, or $C_1$-$C_6$ alkylene substituted with ether group, $R_5$ is O or NH, $R_6$ is $C_1$-$C_6$ alkylene group or $C_1$-$C_6$ alkylene substituted with ether group, $R_7$ is H, $C_1$-$C_6$ alkylene group or $C_1$-$C_6$ alkylene substituted with ether group, $R_8$ is a residue of reactive functional group with hydroxyl group, carboxyl group, epoxy group or acid anhydride group, and n is a integer of 10 to 100.

In an embodiment of the present invention, the second siloxane macromer can be represented by the following formula (IV-1):

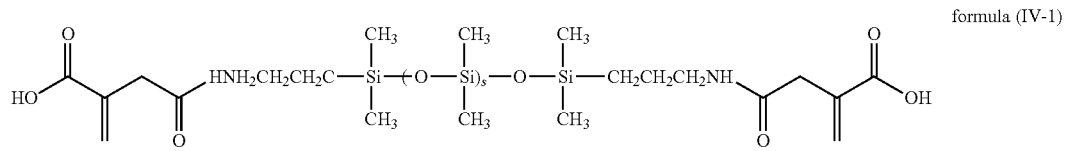

formula (IV-1)

wherein in formula (IV-1), the s is an integer of 10 to 100.

In an embodiment of the present invention, the hydrophilic monomer can be but not limited to, N-vinylpyrrolidone (NVP), 2-hydroxyethyl methacrylate (HEMA), N,N-dimethylacrylamide (DMA), methyl acrylic acid (MAA), acrylic acid, glycidyl methacrylate (GMA), (methyl)acrylamide, 2-(N,N-dimethylamino)ethyl methacrylate (DMAEMA), vinyl acetate, 2-(Dimethylamino)ethyl methacrylate, N-acrylolmorpholine and a combination thereof.

Besides, the initiator suitably used in conventional for manufacturing contact lenses can be used in the composition of the present invention, can be a thermal initiator or a photoinitiator. The suitable thermal initiator, can be not limited to, such as, for example, azobisisoheptonitrile, 2,2'-azobis(isobutyronitrile) (AIBN), 2,2'-azobis(2,4-dimethylvaleronitrile), 2,2'-azobis(2-methyl-propanenitrile), 2,2'-azobis(2-methyl-butanenitrile). The suitable photoinitiator, can be not limited to, such as, for example, 2-Hydroxy-2-methylpropiophenone, 1-Hydroxycyclohexyl phenyl ketone, 2,2-Dimethoxy-2-phenylacetophenone, Benzoin methyl ether, 2,2'-azobis-isobutyronitrile or 2,2-Diethoxyacetophenone.

In the composition for fabricating contact lenses aforementioned, the first siloxane macromer is present at an amount of 30 to 60 parts by weight, the second siloxane macromer is present at an amount of 1 to 15 parts by weight, the hydrophilic monomer is present at an amount of 30 to 65 parts by weight, the fluoro-containing ether monomer is present at an amount of 0.1 to 0.3 parts by weight and the initiator is present at an amount of 0.1 to 1 parts by weight based on the total amount of the composition.

In an embodiment of the present invention, the composition for fabricating contact lenses further includes a crosslinking agent, UV-blocking agent, dye, a UV-blocking agent and a combination of. Moreover, the crosslinking agent suitably used in conventional compositions for manufacturing contact lenses can be used in the method of the present invention, such as, for example, ethylene glycol dimethacrylate (EGDMA), tetraethylene ethylene glycol dimethacrylate (TEGDMA), tetraethylene ethylene glycol dimethacrylate (TrEGDMA), Poly(ethylene glycol)dimethacrylate, trimethylolpropane trimethacrylate (TMPTA), vinyl methacrylate, ethylenediamine dimethyl acrylamide, glycerol dimethacrylate, triallyisoeyanurate or triallyl cyanurate.

According to an aspect of the present invention, a composition for fabricating contact lenses comprises a fluoro-containing ether monomer represented by the formula (I-1); a first siloxane macromer represented by the formula (II) and a second siloxane macromer represented by the formula (IV-1):

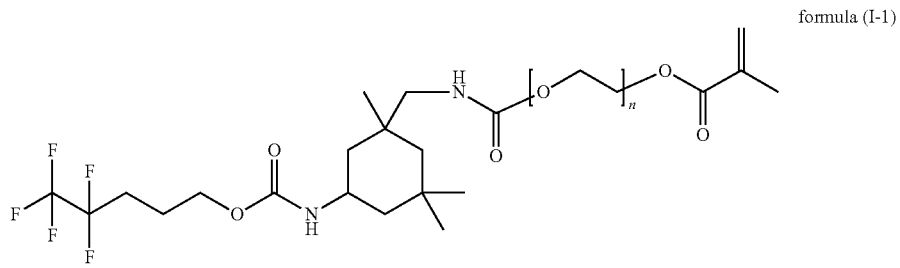

formula (I-1)

wherein in formula (I-1), n is an integer of 3 to 40.

In the embodiment of the invention, the hydrophilic monomer is a combination of HEMA and NVP or a combination of a NVP, HEMA and DMA. According to an aspect of the present invention, a composition for fabricating contact lenses comprises a fluoro-containing ether monomer represented by the formula (I-1), a first siloxane macromer represented by the formula (III) and a second siloxane macromer represented by the formula (IV-1). In the embodiment of the invention, the hydrophilic monomer is a combination of a NVP, HEMA and DMA.

According to an aspect of the present invention, a composition for fabricating contact lenses comprises a fluoro-containing ether monomer represented by the formula (I-2); a first siloxane macromer represented by the formula (II) and a second siloxane macromer represented by the formula (IV-1):

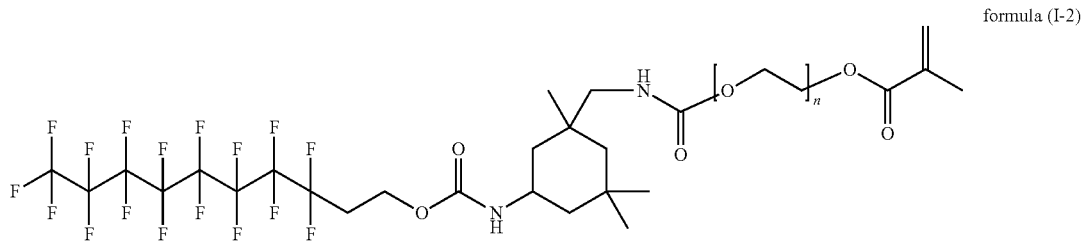

formula (I-2)

wherein in formula (I-2), n is an integer of 3 to 40.

In the embodiment of the invention, the hydrophilic monomer is a combination of DMA, HEMA and NVP, a combination of HEMA and DMA, or a combination of NVP and HEMA.

In an embodiment of the invention, a composition for fabricating contact lenses comprises a fluoro-containing ether monomer represented by the formula (I-2); a first siloxane macromer represented by the formula (III) and a second siloxane macromer represented by the formula (IV-1). In the embodiment of the invention, the hydrophilic monomer is a combination of HEMA and DMA.

In an embodiment of the invention, a composition for fabricating contact lenses comprises a fluoro-containing ether monomer represented by the formula (I-3); a first siloxane macromer represented by the formula (II) and a second siloxane macromer represented by the formula (IV-1):

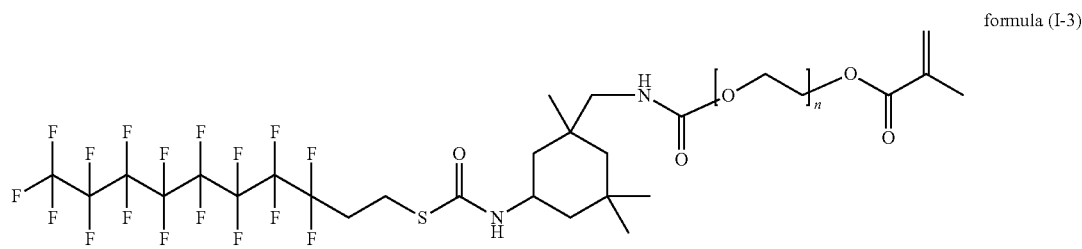

formula (I-3)

wherein in formula (I-3), n is an integer of 3 to 40.

In the embodiment of the invention, the hydrophilic monomer is a combination of HEMA and NVP.

In an embodiment of the invention, a composition for fabricating contact lenses comprises a fluoro-containing ether monomer represented by the formula (I-3); a first siloxane macromer represented by the formula (III) and a second siloxane macromer represented by the formula (IV-1). In the embodiment of the invention, the hydrophilic monomer is a combination of HEMA and DMA.

According to another aspect of the present invention, a composition for fabricating contact lenses comprises a fluoro-containing ether monomer aforementioned; at least one hydrophilic monomer aforementioned; an initiator aforementioned and a crosslinking agent aforementioned. In the embodiment of the invention, the hydrophilic monomer is a combination of NVP, HEMA and MAA.

In the composition for fabricating contact lenses, the hydrophilic monomer is present at an amount of 100 parts by weight, the fluoro-containing ether monomer is present at an amount of 0.1 to 0.3 parts by weight, the crosslinking agent is present at an amount of 0.5 to 1.0 parts by weight, and the initiator is present at an amount of 0.1 to 1 parts by weight based on the total amount of the composition.

According to a further another aspect of the present invention, a method for fabricating contact lenses is provided. The present method can comprise but not limited to the following steps (a) to (b):

In step (a), a first siloxane macromer, a second siloxane macromer, at least one hydrophilic monomer, fluoro-containing ether monomer and an initiator are mixed to form a mixture. To simplify the description, the first siloxane macromer, the second siloxane macromer, the hydrophilic monomer, the fluoro-containing ether monomer and the initiator mentioned above didn't describe in detail.

In the mixture, the first siloxane macromer is present at an amount of 30 to 60 parts by weight, the second siloxane macromer of is present at an amount of 1 to 15 parts by weight, the hydrophilic monomer is present at an amount of 30 to 65 parts by weight, the fluoro-containing ether monomer is present at an amount of 0.1 to 0.3 parts by weight, and the initiator is present at an amount of 0.1 to 1 parts by weight based on the total amount of the mixture.

In addition, the mixture further includes solvent, a crosslinking agent, a dye, a UV-blocking agent and a combination of. The solvent is for example, such as ethanol or hexanol.

In step (b), the mixture is injected into a mold of contact lens and conducted a UV irradiating treatment or a thermal treatment to form contact lenses.

The thermal treatment is conducted at temperature in the range between about 60° C. to about 120° C., and the reaction time is in the range from about 1 hour to 12 hours. In an embodiment of the method of the present invention, the thermal treatment is conducted at 80° C. for 10 hours.

After forming contact lenses, the method of the present invention further comprises a hydration treatment. In an embodiment of the method of the present invention, the hydration treatment comprises but not limited to the following steps.

Firstly, the contact lenses are soaked solvent, for example, isopropyl alcohol or ethanol, then soaked in water, and finally soaked in a buffer solution to reach equilibrium. The buffer solution is, for example, a buffered saline.

According to a further another aspect of the present invention, contact lenses obtained by the method mentioned above is provided.

From the physical property test, the oxygen permeability (DK) of the contact lenses according to the present invention is more than 90, and preferably more than 150. By comparison with contact lenses with fluoro-containing ether monomer free, the contact lenses made of fluoro-containing ether monomer can actually enhance oxygen permeability (DK) of contact lenses.

Moreover, the water content of the contact lenses according to the present invention is more than 30%. In another embodiment of the present invention, the water content of the contact lenses is in the range about 30% to 55%.

The present invention will be explained in further detail with reference to the examples. However, the present invention is not limited to these examples.

EXAMPLE

The Preparation of First Siloxane Macromer (A1)

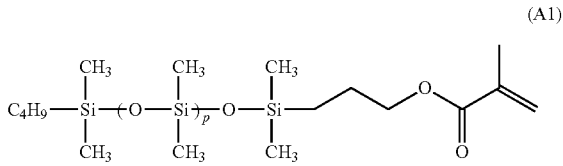

(A1)

The siloxane macromer (A1), commercial code, MCR-M11 (the number average molecular weight is about 1000), is obtained from Gelest.

The Preparation of First Siloxane Macromer (A2)

4.44 g of isophorone diisocyanate, 0.0025 g of dibutyltin dilaurate as the catalyst, and 40 mL of methylene chloride were added to a flask, and the solution was stirred under a stream of nitrogen. Then, 20 g of monocarbinol terminated polydimethylsiloxane (commercial code, MCR-C12, the number average molecular weight is about 1000, from Gelest) was accurately weighed and added dropwise to the solution over about 1 hour. After the solution reacting at room temperature for 12 hours, another 0.0025 g of dibutyltin dilaurate and 7.2 g of polyethylene glycol monomethacrylate (the number average molecular weight is about 526) were accurately weighed and added dropwise to the solution over about 1 hour. After the solution reacting at room temperature for another 12 hours, the resulting reaction product was washed with a large amount of water, and then dehydrated and filtered to obtain a raw product. Then, the methylene chloride was evaporated to obtain a siloxane macromer (A2) (the number average molecular weight is about 1700).

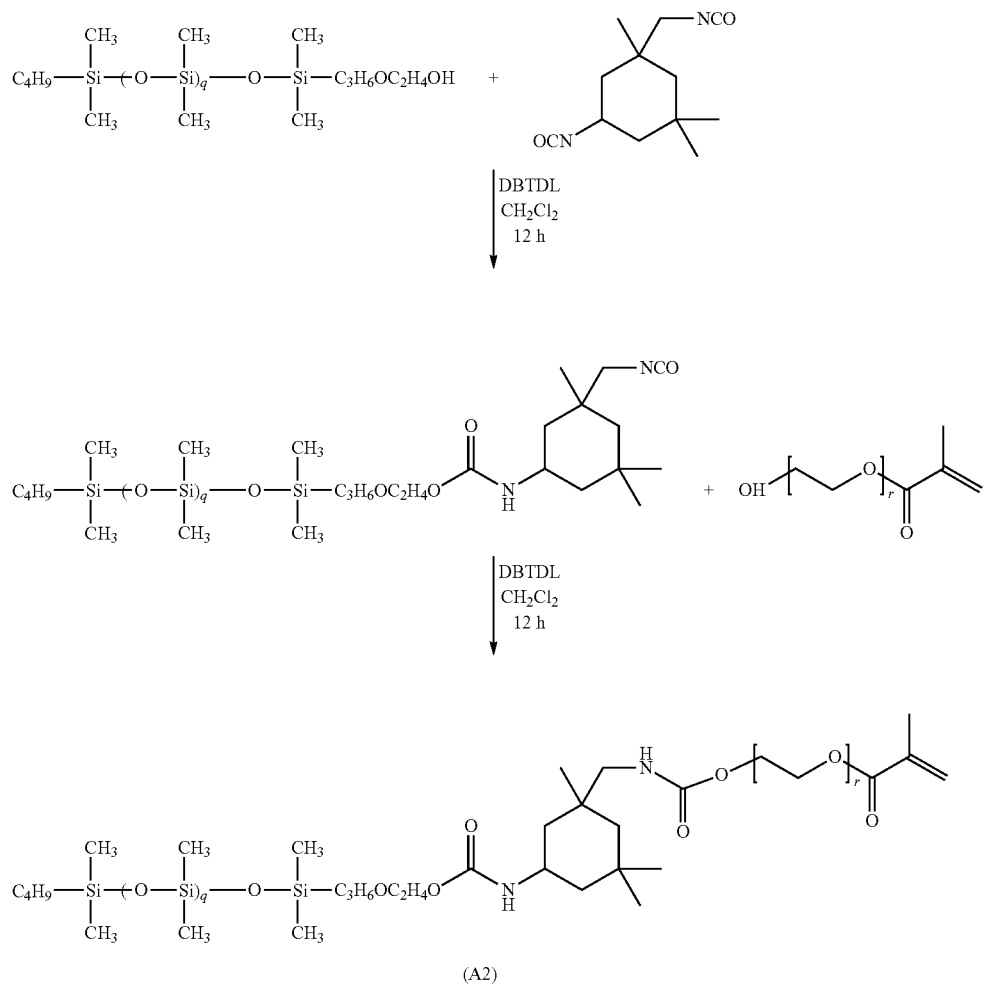

The Preparation of Second Siloxane Macromer (B)

20 g (0.02 mole) of aminopropyl terminated polydimethylsiloxane (commercial code DMS-A12, the number average molecular weight is about 1000, from Gelest), 4.5 g of itaconic anhydride (0.040 mole) and 40 mL of methylene chloride were added to a flask to form a solution, then the solution was stirred at room temperature. After the solution stirring at room temperature for 12 hours, the resulting reaction product was washed with a large amount of water, and then dehydrated and filtered to obtain a raw product. Then, the methylene chloride was evaporated to obtain a siloxane macromer (B) (the number average molecular weight is about 1200).

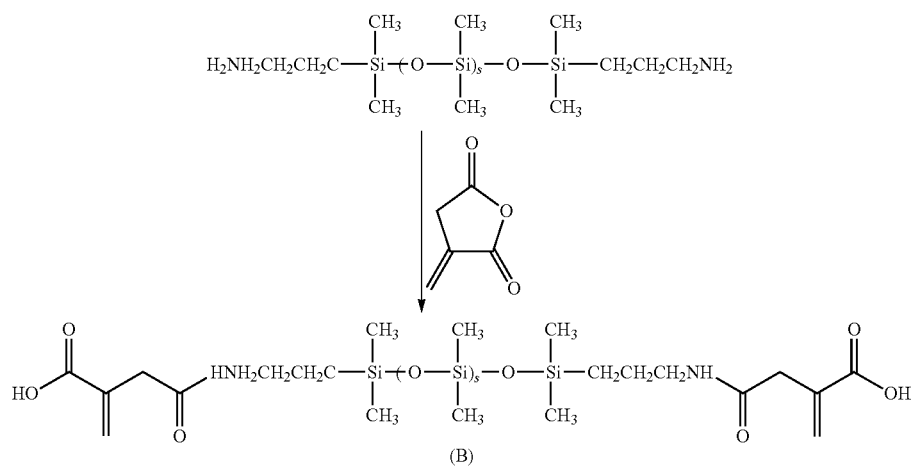

The Properties of Siloxane Macromer (B)
NMR Spectroscopy:
The results of analysis of ¹H-NMR exhibited as follows:
1H-NMR (400 MHz, CDCl₃), δ 6.36 (s, 1H), 5.82 (s, 1H), 3.39-3.21 (m, 4H), 1.62-1.42 (m, 2H), 062-0.47 (m, 2H), 0.19-0.02 (Si—CH₃).
IR Spectroscopy:
(1) Absorption bands derived from Si—CH₃ at 802 cm⁻¹ and 1259 cm⁻¹.
(2) Absorption bands derived from Si—O—Si at 1032 cm⁻¹ and 1100 cm⁻¹.

The Preparation of Fluoro-Containing Ether Monomer (I-1)

12 g of isophorone diisocyanate, 0.0012 g of dibutyltin dilaurate as the catalyst, and 40 mL of methylene chloride were added to a flask, and the solution was stirred under a stream of nitrogen. Then, 10 g of 4,4,5,5,5-Pentafluoro-1-pentanol was accurately weighed and added dropwise to the solution over about 20 mins. After the reaction at room temperature for 6 hours, another 0.0012 g of dibutyltin dilaurate and 20 g polyethylene glycol monomethacrylate (the number average molecular weight is about 360) were accurately weighed and added dropwise to the solution over about 20 mins. After the solution stirring for 12 hours, the resulting reaction product was washed with a large amount of water, and then dehydrated and filtered to obtain a raw product. Then, the methylene chloride was evaporated to obtain a fluoro-containing ether monomer (I-1) (the number average molecular weight is about 745).

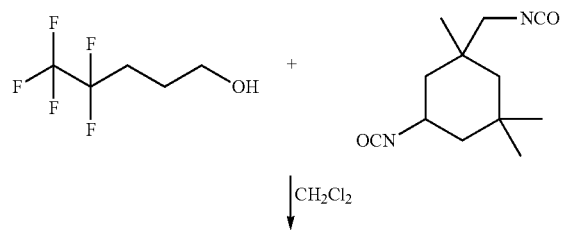

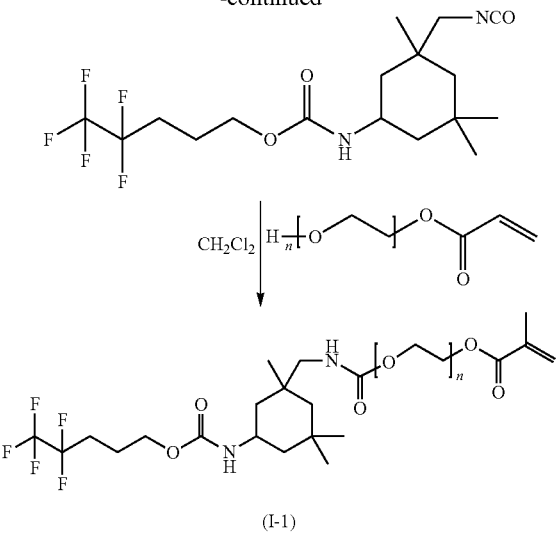

(I-1)

The Preparation of Fluoro-Containing Ether Monomer (I-2)

12 g of isophorone diisocyanate, 0.0012 g of dibutyltin dilaurate as the catalyst, and 40 mL of methylene chloride were added to a flask, and the solution was stirred under a stream of nitrogen. Then, 25 g of 1H,1H,2H,2H-Perfluoro-1-decanol was accurately weighed and added dropwise to the solution over about 20 mins. After the solution reacting at room temperature for 6 hours, another 0.0012 g of dibutyltin dilaurate and 20 g polyethylene glycol monomethacrylate (the number average molecular weight is about 360) were accurately weighed and added dropwise to the solution over about 20 mins. After the solution stirring for 12 hours, the resulting reaction product was washed with a large amount of water, and then dehydrated and filtered to obtain a raw product. Then, the methylene chloride was evaporated to obtain a fluoro-containing ether monomer (1-2) (the number average molecular weight is about 1046).

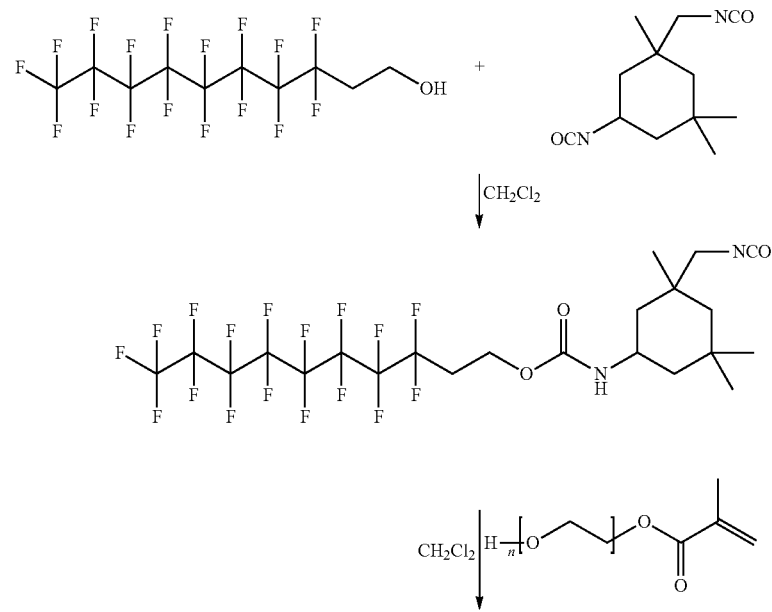

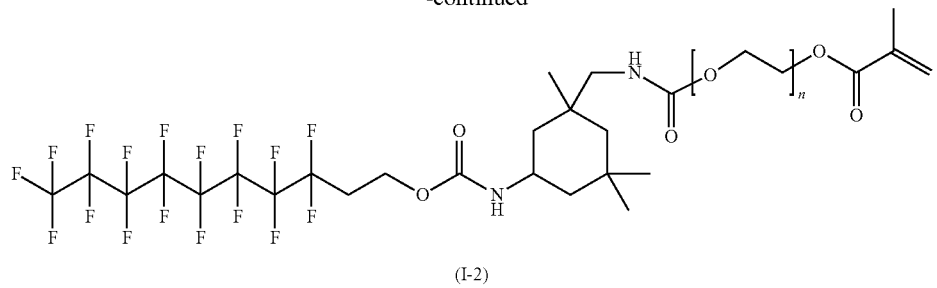

(I-2)

The Preparation of Fluoro-Containing Ether Monomer (I-3)

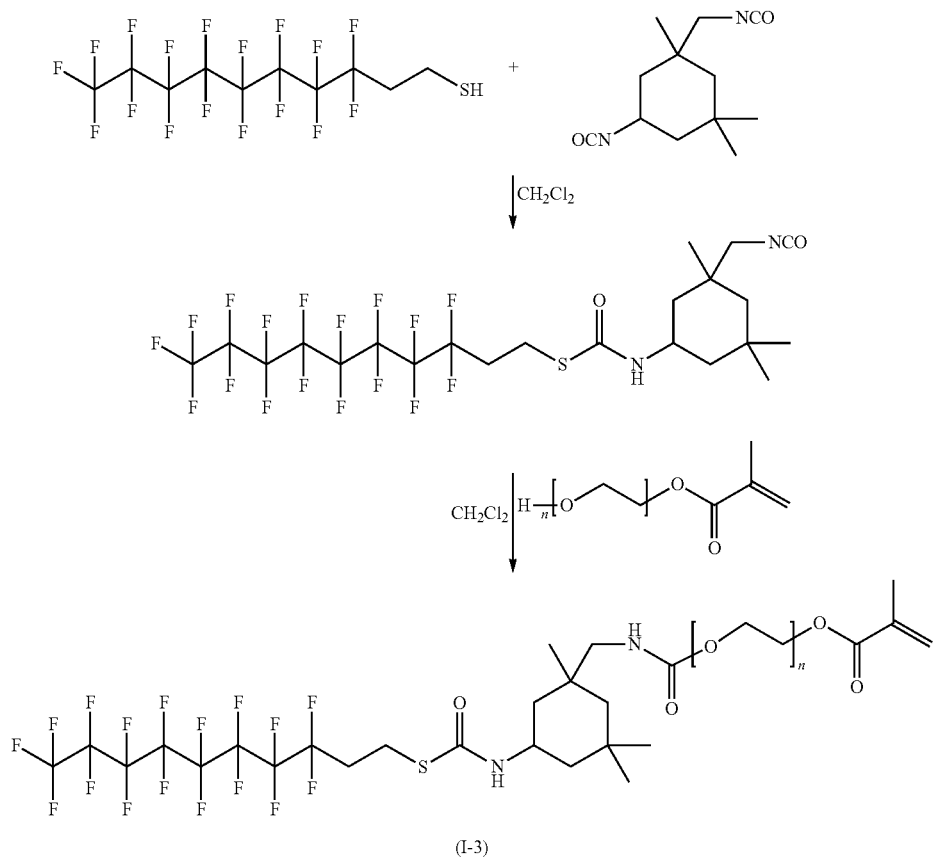

(I-3)

12 g of isophorone diisocyanate and 40 mL of methylene chloride were added to a flask and the solution was stirred under a stream of nitrogen. Then, 26 g of 1H,1H,2H,2H-perfluoodecanethiol was accurately weighed and added dropwise to the solution over about 20 mins. The reaction temperature is controlled at 60° C. for 6 hours. Then, the flask is cooled down to room temperature and another 0.0012 g of dibutyltin dilaurate and 20 g polyethylene glycol monomethacrylate (the number average molecular weight is about 360) were accurately weighed and added dropwise to the solution over about 12 hrs. The resulting reaction product was washed with a large amount of water, and then dehydrated and filtered to obtain a raw product. Then, the methylene chloride was evaporated to obtain a fluoro-containing ether monomer (I-3) (the number average molecular weight is about 1060).

The Properties of Fluoro-Containing Ether Monomer (I-3)
NMR Spectroscopy
(1) A peak of methyl protons derived from isophorone diisocyanate at around from 0.7 ppm to 1.1 ppm.
(2) A peak of methyl protons of methacryloy group at around 1.88 ppm.
(3) A peak of vinyl protons of methacryloy group at around 5.54 ppm and 6.09 ppm.
(4) A peak derived from $CH_2$—F at around from 1.60 ppm to 1.71 ppm, 2.20 ppm to 2.04 ppm, 3.71 ppm to 3.65 ppm.
IR Spectroscopy
(1) Absorption bands derived from Si—$CH_3$ at 802 $cm^{-1}$ and 1259 $cm^{-1}$.
(2) Absorption bands derived from Si—O—Si at 1032 $cm^{-1}$ and 1100 $cm^{-1}$.

(3) Absorption bands derived from C=O of methacryloy group at 1720 cm$^{-1}$.

The Preparation of the Contact Lenses

The Preparation of the Contact Lenses of Example 1

A siloxane macromer (A1), a siloxane macromer (B), N-vinylpyrrodine (NVP), 2-hydroxyethyl methacrylate (HEMA), N,N-dimethylacrylamide (DMA), fluoro-containing ether monomer (I-1), a thermal initiator, 2-2'-azobis(isobutyronitrile) (AIBN) and hexanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 2

A siloxane macromer (A1), a siloxane macromer (B), N-vinylpyrrodine (NVP), 2-hydroxyethyl methacrylate (HEMA), a thermal initiator, 2-2'-azobis(isobutyronitrile) (AIBN), fluoro-containing ether monomer (I-1) and hexanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 3

A siloxane macromer (A2), a siloxane macromer (B), N-vinylpyrrodine (NVP), 2-hydroxyethyl methacrylate (HEMA), N,N-dimethylacrylamide (DMA), a thermal initiator, 2-2'-azobis(isobutyronitrile) (AIBN), fluoro-containing ether monomer (I-1) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 4

A siloxane macromer (A1), a siloxane macromer (B), N-vinylpyrrodine (NVP), 2-hydroxyethyl methacrylate (HEMA), N,N-dimethylacrylamide (DMA), a thermal initiator, 2-2'-azobis(isobutyronitrile) (AIBN), fluoro-containing ether monomer (I-2) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 5

A siloxane macromer (A2), a siloxane macromer (B), N,N-dimethylacrylamide (DMA), 2-hydroxyethyl methacrylate (HEMA), a thermal initiator, 2-2'-azobis(isobutyronitrile) (AIBN), fluoro-containing ether monomer (I-2) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 6

A siloxane macromer (A1), a siloxane macromer (B), 2-hydroxyethyl methacrylate (HEMA), N,N-dimethylacrylamide (DMA), a thermal initiator, 2-2'-azobis(isobutyronitrile) (AIBN), fluoro-containing ether monomer (I-2) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 7

A siloxane macromer (A1), a siloxane macromer (B), N-vinylpyrrodine (NVP), 2-hydroxyethyl methacrylate (HEMA), a thermal initiator, 2-2'-azobis(isobutyronitrile) (AIBN), fluoro-containing ether monomer (I-3) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 8

A siloxane macromer (A1), a siloxane macromer (B), N-vinylpyrrodine (NVP), 2-hydroxyethyl methacrylate (HEMA), a thermal initiator, 2-2'-azobis(isobutyronitrile) (AIBN), fluoro-containing ether monomer (I-3) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 9

A siloxane macromer (A2), a siloxane macromer (B), 2-hydroxyethyl methacrylate (HEMA), N,N-dimethylacrylamide (DMA), a thermal initiator, 2-2'-azobis(isobutyronitrile) (AIBN), fluoro-containing ether monomer (I-3) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 10

A siloxane macromer (A1), a siloxane macromer (B), 2-hydroxyethyl methacrylate (HEMA), N-vinylpyrrodine (NVP), a thermal initiator, 2-2'-azobis(isobutyronitrile) (AIBN), fluoro-containing ether monomer (I-1) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 11

A siloxane macromer (A1), a siloxane macromer (B), N-vinylpyrrodine (NVP), 2-hydroxyethyl methacrylate (HEMA), a thermal initiator, 2-2'-azobis(isobutyronitrile) (AIBN), fluoro-containing ether monomer (I-2) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Example 12

A siloxane macromer (A1), a siloxane macromer (B), N-vinylpyrrodine (NVP), 2-hydroxyethyl methacrylate (HEMA), a thermal initiator, 2-2'-azobis(isobutyronitrile) (AIBN), fluoro-containing ether monomer (I-3) and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Comparative Example 1

A siloxane macromer (A1), a siloxane macromer (B), N-vinylpyrrodine (NVP), 2-hydroxyethyl methacrylate (HEMA), N,N-dimethylacrylamide (DMA), a thermal initiator, 2-2'-azobis(isobutyronitrile) (AIBN), and hexanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Comparative Example 2

A siloxane macromer (A1), a siloxane macromer (B), N-vinylpyrrodine (NVP), 2-hydroxyethyl methacrylate (HEMA), a thermal initiator, 2-2'-azobis(isobutyronitrile) (AIBN), and hexanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

The Preparation of the Contact Lenses of Comparative Example 3

A siloxane macromer (A2), a siloxane macromer (B), N-vinylpyrrodine (NVP), 2-hydroxyethyl methacrylate (HEMA), N,N-dimethylacrylamide (DMA), a thermal initiator, 2-2'-azobis(isobutyronitrile) (AIBN), and ethanol were mixed at the amounts shown in Table 1 and stirred about 1 hour.

Then, the mixtures were injected into a mold of contact lens made of polypropylene (PP) and heated to initiate the radical polymerization thereof at 80° C. for 10 hrs.

After the polymerization was completed, the mold was immersed in isopropyl alcohol solution for 1 hour and the resulting molded lens was taken out of the mold. The resulting lens was immersed in heated water for 4 hrs and then immersed in a buffer solution to reach equilibrium.

Physical Property Tests

The results of physical property tests of Comparative Example 1-Comparative Example 3, and Example 1-Example 12 of the present invention were shown as the following Table 2.

As shown in Table 2, Examples 1 to Example 12 of the present invention have more excellent oxygen permeability than Comparative Example 1 to Comparative Example 3 with fluoro-containing ether monomer free. In addition, the water content of Example 1 to Example 12 are about 33% to 54%, the modulus of Example 1 to Example 12 are about 0.35 MPa to 0.65 MPa, the tension of Example 1 to Example 12 are about 15 g to 83 g, the oxygen permeability (DK) of Example 1 to Example 12 are about 93 to 166.

While the invention has been described by way of example(s) and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

TABLE 1

The composition of contact lenses of Example 1-Example 12 and Comparative Example 1-3

| Composition | Function | Abbr. | Comparative Example (wt %) | | | Example (wt %) | | | | | | | | | | | |
|---|---|---|---|---|---|---|---|---|---|---|---|---|---|---|---|---|---|
| | | | 1 | 2 | 3 | 1 | 2 | 3 | 4 | 5 | 6 | 7 | 8 | 9 | 10 | 11 | 12 |
| First siloxane macromer | Siloxane macromer (A1) | A1 | 34.5 | 41.8 | | 34.5 | 41.8 | | 44.4 | | 50.1 | 35.4 | 38.8 | | 38 | 38 | 38 |
| | Siloxane macromer (A2) | A2 | | | 47.5 | | | 47.5 | | 38.6 | | | | 38.6 | | | |
| Second siloxane macromer | Siloxane macromer (B) | B | 7.1 | 6.3 | 7.1 | 7.1 | 6.3 | 7.1 | 5.8 | 5.8 | 5.5 | 7.2 | 7.3 | 5.8 | 10.2 | 10.2 | 10.2 |
| Hydrophilic monomer | N-vinylpyrrodine | NVP | 47.2 | 44.9 | 28.6 | 47.2 | 44.9 | 28.5 | 18.1 | | | 47.3 | 48.5 | | 36.7 | 36.7 | 36.7 |
| | 2-hydroxyethyl methacrylate | HEMA | 6.5 | 6.3 | 8.3 | 6.5 | 6.3 | 8.3 | 13.5 | 13.5 | 13.5 | 9.5 | 4.8 | 13.5 | 14.5 | 14.5 | 14.5 |
| | N,N-dimethyl acrylamide | DMA | 4.7 | | 8.3 | 4.7 | | 8.3 | 17.9 | 41.5 | 30.3 | | | 41.5 | | | |
| fluoro-containing ether monomer | fluoro-containing ether monomer (I-1) | I-1 | | | | 0.1 | 0.2 | 0.2 | | | | | | | 0.2 | | |
| | fluoro-containing ether monomer (I-2) | I-2 | | | | | | | 0.3 | 0.2 | 0.2 | | | | | 0.2 | |
| | fluoro-containing ether monomer (I-3) | I-3 | | | | | | | | | | 0.2 | 0.2 | 0.3 | | | 0.2 |
| thermal initiator | 2-2-azobis(iso butyronitrile) | AIBN | 0.7 | 0.7 | 0.7 | 0.7 | 0.7 | 0.7 | 0.6 | 0.6 | 0.6 | 0.6 | 0.6 | 0.6 | 0.6 | 0.6 | 0.6 |
| Solvent | Hexanol | HeOH | 25 | 25 | | 25 | 25 | | | | | | | | | | |
| | Ethanol | EtOH | | | 25 | | | 25 | 25 | 10 | 10 | 20 | 25 | 25 | 10 | 20 | 20 | 20 |

TABLE 2

The physical properties of contact lenses of Example 1-12 and Comparative Example 1-3

| Item | Comparative Example | | | Example | | | | | | | | | | | |
|---|---|---|---|---|---|---|---|---|---|---|---|---|---|---|---|
| | 1 | 2 | 3 | 1 | 2 | 3 | 4 | 5 | 6 | 7 | 8 | 9 | 10 | 11 | 12 |
| Water content (%) | 34.8 | 55.5 | 55.5 | 34.9 | 40.2 | 41.8 | 43.3 | 53.1 | 41.6 | 34.4 | 51.5 | 50.4 | 44.5 | 41.5 | 42.2 |
| Modulus (Mpa) | 0.63 | 0.39 | 0.34 | 0.39 | 0.42 | 0.38 | 0.65 | 0.42 | 0.64 | 0.63 | 0.58 | 0.39 | 0.59 | 0.65 | 0.65 |
| Tension (g) | 16.6 | 16.2 | 17.1 | 15 | 21 | 19 | 60 | 53 | 83 | 17 | 37 | 55 | 41 | 38 | 40 |
| Oxygen permeability (Dk) | 81 | 88 | 89 | 94 | 150 | 155 | 157 | 93 | 166 | 103 | 101 | 110 | 142 | 157 | 155 |

What is claimed is:

1. A contact lens which is fabricated by a composition for fabricating contact lenses comprising:

a fluoro-containing ether monomer represented by the following formula (I):

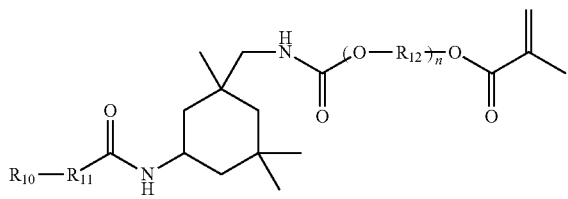

formula (I)

wherein in formula (I), $R_{10}$ is fluoroalkyl group $C_xF_yH_z$, wherein x is an integer of 2 to 20, y is an integer of 5 to 30, and y+z=2x+1; $R_{11}$ is a oxygen, nitrogen or sulfur;

$R_{12}$ is $C_1$-$C_3$ alkylene group; and n is an integer of 3 to 40;

at least one hydrophilic monomer;

at least one siloxane macromer; and an initiator.

2. The composition for fabricating contact lenses according to claim 1, wherein the siloxane macromer comprising:

a first siloxane macromer represented by the following formula (II) or a siloxane macromer represented by the following formula (III):

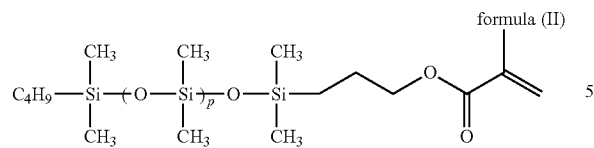

formula (II)

wherein in formula (II), p is an integer of 4 to 80; and

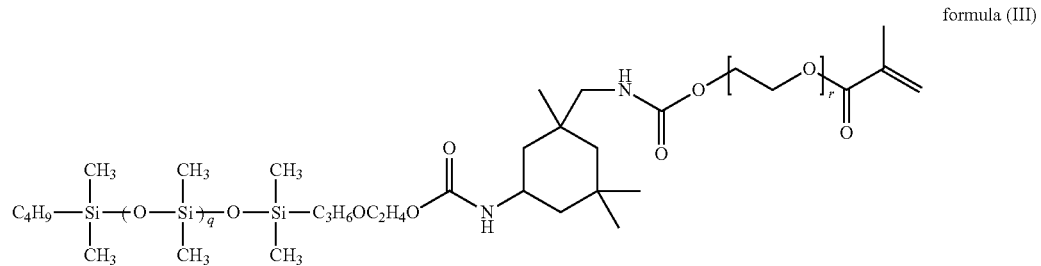

formula (III)

in formula (III), q is an integer of 4 to 80 and r is an integer of 3 to 40, a second siloxane macromer, represented by the following formula (IV), having the number average molecular weight in a range of 1,000 to 10,000 and the second siloxane macromer with cross-linking functional groups,

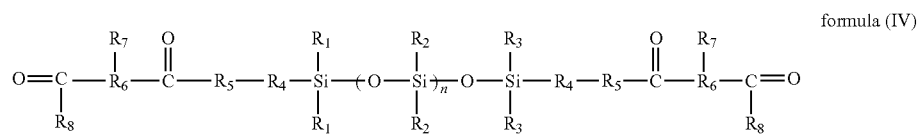

formula (IV)

wherein $R_1$, $R_2$ and $R_3$ are independently $C_1$-$C_4$ alkyl groups, $R_4$ is $C_1$-$C_6$ alkenylene group, $C_1$-$C_6$ alkylene group, or $C_1$-$C_6$ alkylene substituted with ether group, $R_5$ is O or NH, $R_6$ is $C_1$-$C_6$ alkylene group or $C_1$-$C_6$ alkylene substituted with ether functional group, $R_7$ is H, $C_1$-$C_6$ alkylene group or $C_1$-$C_6$ alkylene substituted with ether group, $R_8$ is a residue of reactive functional group with hydroxyl group, carboxyl group, epoxy group or acid anhydride group, and n is a integer of 10 to 100.

3. The composition for fabricating contact lenses according to claim 2, wherein the first siloxane macromer is present at an amount of 30 to 60 parts by weight, the second siloxane macromer of is present at an amount of 1 to 15 parts by weight, the hydrophilic monomer is present at an amount of 30 to 65 parts by weight, the hydrophilic fluorine-containing ether monomer is present at an amount of 0.1 to 0.3 parts by weight, and the initiator is present at an amount of 0.1 to 1 parts by weight based on the total amount of the composition.

4. The composition for fabricating contact lenses according to claim 1, wherein the hydrophilic monomer is selected from the group consisting of N-vinylpyrrolidone (NVP), 2-hydroxyethyl methacrylate (HEMA), N,N-dimethylacrylamide (DMA), methyl acrylic acid, acrylic acid, glycidyl methacrylate (GMA), (methyl)acrylamide, 2-(N,N-dimethylamino)ethyl methacrylate (DMAEMA), vinyl acetate, 2-(dimethylamino)ethyl methacrylate, N-acrylolmorpholine and a combination thereof.

5. The composition for fabricating contact lenses according to claim 1, wherein in formula (I), $R_{10}$ is $C_5F_5H_6$ or $C_{10}F_{17}H_4$; $R_{11}$ is oxygen or sulfur and $R_{12}$ is $CH_2CH_2$.

* * * * *